US008222380B2

(12) United States Patent  
Ludescher et al.

(10) Patent No.: US 8,222,380 B2
(45) Date of Patent: Jul. 17, 2012

(54) AMORPHOUS TELITHROMYCIN COMPOUND

(75) Inventors: Johannes Ludescher, Breitenbach (AT); Ulrich Griesser, Axams (AT); Christoph Langes, Innsbruck (AT)

(73) Assignee: Sandoz AG, Basel (CH)

( * ) Notice: Subject to any disclaimer, the term of this patent is extended or adjusted under 35 U.S.C. 154(b) by 226 days.

(21) Appl. No.: 12/159,939

(22) PCT Filed: Jan. 4, 2007

(86) PCT No.: PCT/EP2007/000036
§ 371 (c)(1),
(2), (4) Date: Jul. 2, 2008

(87) PCT Pub. No.: WO2007/077219
PCT Pub. Date: Jul. 12, 2007

(65) Prior Publication Data
US 2008/0280841 A1   Nov. 13, 2008

(30) Foreign Application Priority Data
Jan. 6, 2006 (GB) .................................. 0600238.0

(51) Int. Cl.
*C07H 17/08* (2006.01)

(52) U.S. Cl. ........................................................ 536/7.4
(58) Field of Classification Search ............. 536/7.2, 536/7.4
See application file for complete search history.

(56) References Cited

U.S. PATENT DOCUMENTS

| 4,127,647 | A | * | 11/1978 | Sato et al. ..................... 424/115 |
| 5,635,485 | A | * | 6/1997 | Agouridas et al. ............. 514/29 |
| 6,100,404 | A |   | 8/2000 | Agouridas et al. |

FOREIGN PATENT DOCUMENTS

| EP | 0680967 | 11/1995 |
| WO | 2004/080391 | 9/2004 |
| WO | 2005/105821 | 11/2005 |

* cited by examiner

*Primary Examiner* — Elli Peselev
(74) *Attorney, Agent, or Firm* — Luedeka Neely Group, P.C.

(57) ABSTRACT

The present invention relates to stable amorphous 3-De[(2,6-dideoxy-3-C-methyl-3-O-methyl-α-L-ribohexopyranosyl)oxy]-11,12-dideoxy-6-O-methyl-3-oxo-12,11-[oxycarbonyl[[4-[4-(3-pyridinyl)-1H-imidazol-1-yl]butyl]imino]] erythromycin (telithromycin), methods for the preparation thereof, the use of stable amorphous telithromycin in the treatment of bacterial infections and to pharmaceutical compositions comprising stable amorphous telithromycin.

9 Claims, 1 Drawing Sheet

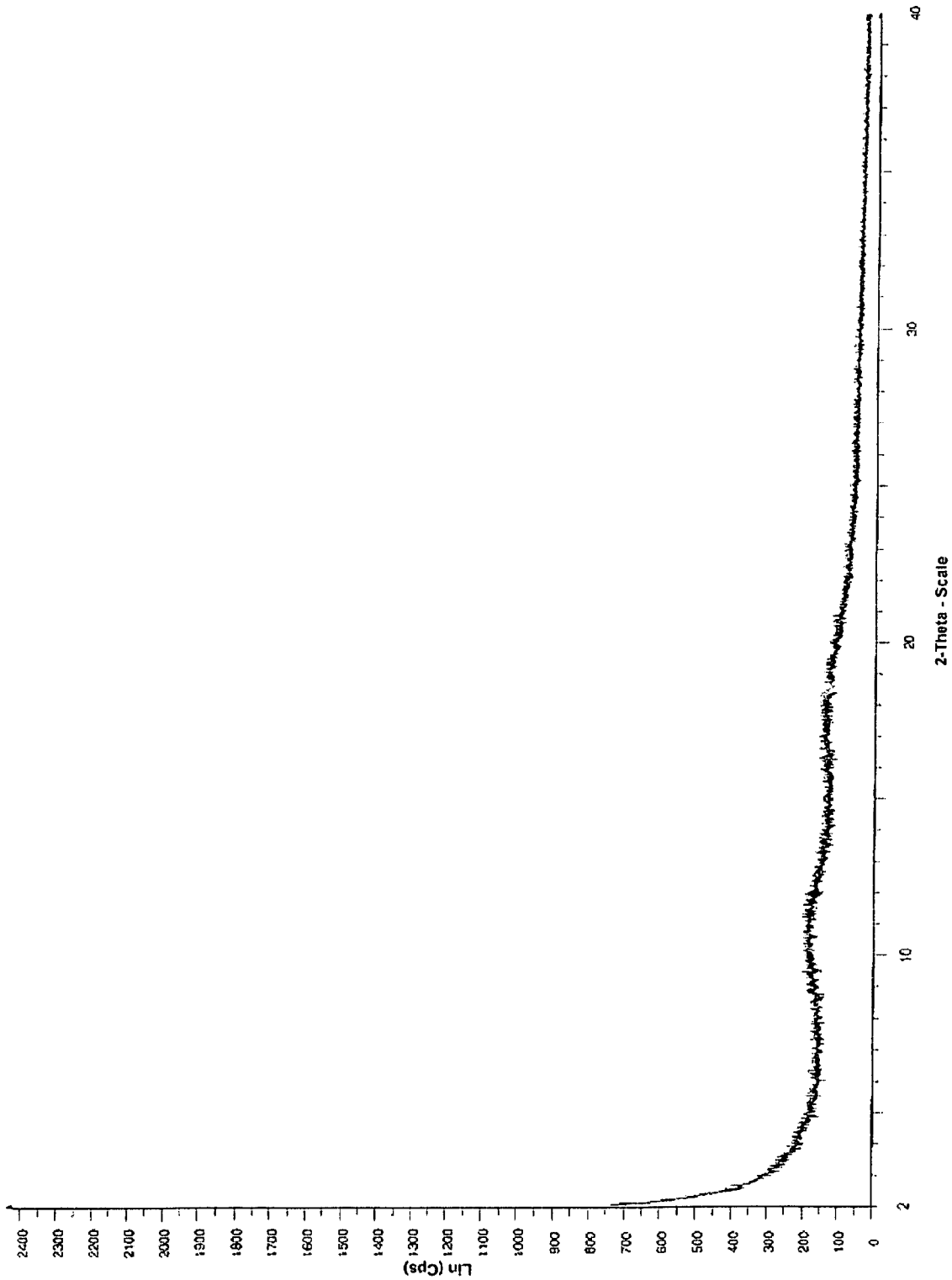

AMORPHOUS TELITHROMYCIN COMPOUND

This application is the National stage of International Application No. PCT/EP07/000,036, filed on Jan. 4, 2007, which claims benefit under 35 U.S.c §119(e) of United Kingdom Patent Application No. 0600238.0 filed on Jan. 6, 2006, the contents of both are incorporated herein by reference in their entirety.

The present invention relates to stable amorphous 3-De[(2,6-dideoxy-3-C-methyl-3-O-methyl-α-L-ribohexopyranosyl)oxy]-11,12-dideoxy-6-O-methyl-3-oxo-12,11-[oxycarbonyl[[4-[4-(3-pyridinyl)-1H-imidazol-1-yl]butyl]imino]]erythromycin (telithromycin), methods for the preparation thereof, the use of stable amorphous telithromycin in the treatment of bacterial infections and to pharmaceutical compositions comprising stable amorphous telithromycin.

Telithromycin, shown as compound (I) below,

Compound (I)

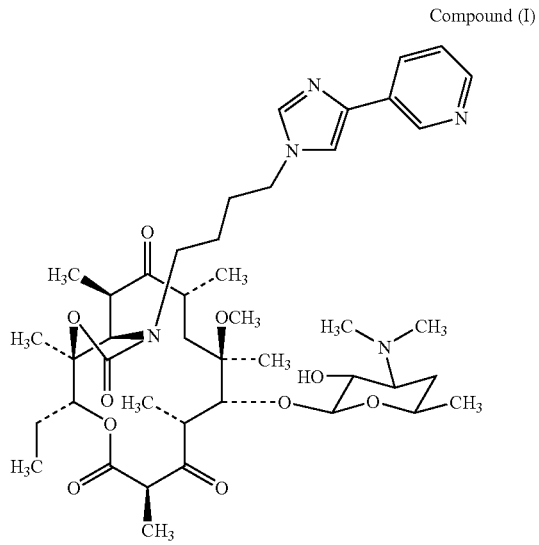

is a semi-synthetic macrolide antibiotic of the ketolide class. Within this group of erythromycin derivatives the L-cladinose residue has been replaced by a 3-keto group. The preparation of telithromycin is described in EP 680967 and U.S. Pat. No. 5,635,485, and its antibiotic effect has been the subject of several research articles, e.g. Denis et al., *Bioorg. Med. Chem. Lett.* 9, 3075 (1999): "*In vitro activity vs. anaerobic bacteria.*" A review of its pharmacological properties can be found in G. Ackermann, A. C. Rodloff, *J. Antimicrob. Chemother.* 51, 497-511 (2003).

Telithromycin is sold in the U.S. as KETEK® in the form of tablets. KETEK® is to be used in the treatment of mild or moderate community-acquired pneumonia, acute exacerbation of chronic bronchitis, acute sinusitis and tonsillitis/pharyngitis caused by group A beta-hemolytic *streptococci*, as an alternative when beta-lactam antibiotics are not appropriate.

The preparation of crystalline forms of telithromycin was first disclosed in EP 680976. There is no amorphous telithromycin available for pharmaceutical compositions.

Amorphous products are in general more soluble and therefore often show improved absorption in humans.

However, amorphous products often are metastable and can return to the stable crystalline state within a few days or weeks. This is exemplified by amorphous novobiocin, which shows very good solubility, but readily returns to the poorly soluble crystalline state.

There is thus a need for a stable amorphous form of telithromycin which is suitable for application in pharmaceutical compositions.

SUMMARY OF THE INVENTION

The present invention provides stable amorphous telithromycin (3-De[(2,6-dideoxy-3-C-methyl-3-O-methyl-α-L-ribohexopyranosyl)oxy]-11,12-dideoxy-6-O-methyl-3-oxo-12,11-[oxycarbonyl[[4-[4-(3-pyridinyl)-1H-imidazol-1-yl]butyl]imino]]erythromycin), methods for the preparation thereof, the use of stable amorphous telithromycin in the treatment of bacterial infections and pharmaceutical compositions comprising stable amorphous telithromycin.

DETAILED DESCRIPTION OF THE INVENTION

The present inventors have surprisingly identified an amorphous form of telithromycin which is stable upon storage. This property is important and proves advantageous for the desired use of telithromycin in pharmaceutical formulations. Moreover, the amorphous form of telithromycin of the invention lends itself to facile coating.

The invention therefore relates to a stable amorphous form of telithromycin (3-De[(2,6-dideoxy-3-C-methyl-3-O-methyl-α-L-ribohexopyranosyl)oxy]-11,12-dideoxy-6-O-methyl-3-oxo-12,11-[oxycarbonyl[[4-[4-(3-pyridinyl)-1H-imidazol-1-yl]butyl]imino]]erythromycin). The stable amorphous form of telithromycin is stable in the amorphous state, as judged by X-ray power diffraction (XRPD), for at least two weeks, like for at least four weeks or for from 8 weeks to 24 months, and even after 8 weeks shows no signs of the presence of crystalline telithromycin as judged by its X-ray powder diffractogram.

In a preferred embodiment, the stable amorphous form of telithromycin is an inert stable amorphous form of telithromycin. By "inert" it is meant that the amorphous form of telithromycin of the invention shows very little degradation upon storage under stress conditions, and that there is an increase in impurity levels as measured by HPLC, the measurement being detailed in example 1, of less than 0.3 area % when stored at 80° C. for 24 hours.

In a preferred embodiment, the inert amorphous form of telithromycin exhibits an increase in impurity levels as measured by HPLC as described above of less than 0.3 area % when stored at 25° C./60% relative humidity for one month, in particular even when stored for 6 months.

The invention further relates to processes for the production of the stable amorphous form of telithromycin of the invention starting from crystalline telithromycin or solutions originating from the synthesis or purification of telithromycin. The telithromycin to be used as starting material can be obtained, e.g., according to the process as described in, e.g., EP 680967.

In one embodiment the process for the production of a stable amorphous form of telithromycin comprises the steps of a) dissolving crystalline telithromycin in a solvent to obtain a telithromycin solution and b1) adding the telithromycin solution obtained from step a) to an antisolvent to obtain a suspension, or b2) adding an antisolvent to the telithromycin solution obtained from step a) to obtain a suspension, c) optionally storing the suspension for a time sufficient to form stable amorphous telithromycin and d) isolating a stable amorphous form of telithromycin.

An antisolvent as used herein is a solvent wherein telithromycin is at most only sparingly soluble, that is at least 30 ml of solvent are necessary to solubilize 1 gram of telithromycin.

A preferred antisolvent is a solvent wherein telithromycin is at most only slightly soluble, that is at least 100 ml of solvent are necessary to solubilize 1 gram of telithromycin. A more preferred antisolvent is a solvent wherein telithromycin is at most only very slightly soluble, that is at least 1000 ml of solvent are necessary to solubilize 1 gram of telithromycin.

In particular crystalline telithromycin is preferably dissolved in an alcohol, for example a $C_1$-$C_4$ alcohol, e.g. methanol, ethanol, n-propanol or butanol; a ketone, e.g. acetone or methylethylketone; a carboxylic ester, e.g. ethylacetate or methylacetate; an ether, e.g. tetrahydrofuran or dioxane; an aromatic hydrocarbon, e.g. toluene; a chlorinated hydrocarbon, e.g. methylenchloride or chloroform, or a polar organic solvent; e.g. an amide, N,N-dimethylformamide, or dimethylsulfoxide and the antisolvent, is e.g. water, an aliphatic acyclic or cyclic hydrocarbon, e.g. pentane, hexane or cyclohexane. For example telithromycin is dissolved in methanol, preferably at ambient temperature. The solution obtained from step a) is then preferably added to an excess of water, even though, of course, the excess of water may also be added to the solution obtained from step a). Preferably the volume of water used is about 1- to 50-fold the volume of solution obtained from step a), more preferably about 5- to 50-fold. It is preferred that the telithromycin solution is added into the water, preferably all of the telithromycin solution is quenched by pouring it into an excess of water. The skilled person will appreciate that the higher the solubility of telithromycin is in the solvent of step a), the more antisolvent is usually to be added in steps b1) or b2).

In an alternative embodiment the present invention relates to a process for the production of a stable amorphous form of telithromycin comprising the steps of a) dissolving crystalline telithromycin in a solvent to obtain a telithromycin solution and b) lyophilizing the solution, preferably after addition or further addition of water.

In particular crystalline telithromycin is preferably dissolved in an alcohol, for example a $C_1$-$C_4$ alcohol, e.g. methanol, ethanol, n-propanol or butanol, a ketone, e.g. acetone or methylethylketone, or an ether, e.g. tetrahydrofuran or dioxane or mixtures thereof optionally also in the presence of an amount of water that still allows dissolution of telithromycin. Water can then be added or further added, and the solution is frozen and lyophilized. The amount of water added depends on the solvent used for the dissolution of telithromycin. Preferably the volume of water used is about half to about 10 fold the volume of the solution used in step a). For example telithromycin is dissolved in methanol, the same volume of water as the amount of methanol used for the dissolution of telithromycin is added, and the solution is frozen and then lyophilized.

In an alternative embodiment the present invention relates to a process for the production of a stable amorphous form of telithromycin comprising the steps of a) dissolving crystalline telithromycin in a solvent or solvent mixture to obtain a telithromycin solution and b) spray drying the solution to obtain stable amorphous telithromycin. The telithromycin solution can be prepared as described above. In particular crystalline telithromycin is preferably dissolved in an alcohol, for example a $C_1$-$C_4$ alcohol, e.g. methanol, ethanol, n-propanol or butanol; a ketone, e.g. acetone or methylethylketone; or an ether, e.g. tetrahydrofuran or dioxane or mixtures thereof optionally also in the presence of an amount of water that still allows dissolution of telithromycin. Water can then be added or further added, and the solution is spray dried. Preferred solvents are $C_1$-$C_4$ alcohols, e.g. ethanol, ketones, e.g. acetone or ethers, e.g. tetrahydrofuran. The ratio of organic solvent to water is in the range from about 10:1 to about 5:1 (v/v). Preferred inlet temperatures in the spray drying process are in the range of 80° C. to about 150° C.

Optionally a pharmaceutical acceptable carrier may be present in the spray drying process. As pharmaceutically acceptable carriers any material described in Encyclopedia of Pharmaceutical Technology (Vol 3, Table 1 on page 345) may be used, but preferably carriers are selected from the group of polyvinylpyrrolidone, silicon dioxide, mannitol, lactose, saccharose, cellulose, methylcellulose, citric acid and cyclodextrin.

The invention further relates to a pharmaceutical composition comprising stable amorphous telithromycin, in particular comprising an inert stable amorphous form of telithromycin.

Preferred pharmaceutical compositions of the invention are oral dosage forms such as tablets, capsules, powders for oral suspension, pills and granules. For example the stable amorphous telithromycin of the invention can be formulated as 700 mg to 1000 mg tablets for oral administration comprising from 200 mg to 500 mg telithromycin, and further corn starch, microcrystalline cellulose, povidine K25, crosscarmellose-sodium, magnesium stearate, lactose monohydrate, talcum, macrogel 8000, hypromellose and titanium dioxide. Further preferred pharmaceutical compositions comprising stable amorphous telithromycin of the invention are film coated tablets of 250 or 500 mg telithromycin, comprising telithromycin, crosscarmellose sodium, pregelatinised starch, microcrystalline cellulose, silicon dioxide, povidone, stearic acid and magnesium stearate as the core and talcum, hydroxypropylcellulose, propylene glycol, sorbitan monooleate, titanium dioxide, sorbic acid, vanillin and chinolin yellow as the coat. Alternative preferred pharmaceutical compositions comprising stable amorphous telithromycin of the invention are extended release film-coated tablets of 250 or 500 mg telithromycin, comprising telithromycin, waterfree citric acid, sodium alginate, sodium-calcium alginate, lactose monohydrate, povidon 30, talcum and stearic acid and magnesium stearate as the core, and hypromellose 6 cps, macrogel 400, macrogel 8000, titanium dioxide, sorbic acid, chinolin yellow and aluminum finish as the coat. Further alternative preferred pharmaceutical compositions comprising stable amorphous telithromycin of the invention are granulates for oral suspension of telithromycin, comprising pellets of telithromycin, carbopol and povidon, which pellets are coated with hydroxypropylmethylcellulosephtalat, castor oil and maltodextrine and which coated pellets are typically suspended in a medium comprising sucrose, potassium sorbate, silicon dioxide, xanthan gum, titanium dioxide, citric acid and fruit aroma. A further alternative preferred pharmaceutical composition comprising stable amorphous telithromycin of the invention is an injectable form of telithromycin; for example telithromycin is solubilized in a slightly acidic environment, for example a water/alcohol mixture in the presence of citric acid, and then buffered to a pharmaceutically acceptable pH, in particular of from pH 5 to pH 8, with for example sodium hydroxide.

The invention further relates to a method of treating bacterial infections in a mammal comprising using stable amorphous telithromycin, in particular comprising an inert stable amorphous form of telithromycin.

The invention further relates to a method of treating bacterial infections in a mammal comprising using a pharmaceutical composition comprising stable amorphous telithromycin of the invention. Preferred bacterial infections are mild or moderate community-acquired pneumonia, acute exacerbation of chronic bronchitis, acute sinusitis and tonsillitis/pharyngitis caused by group A beta-hemolytic *streptococci*, in particular wherein telithromycin is used as an alternative when beta-lactam antibiotics are not appropriate.

DESCRIPTION OF THE FIGURE

The stable amorphous form of telithromycin as obtained according to example 2 was analyzed by X-ray powder diffraction diagrams, measured using an AXS-Bruker D-8 diffractometer (Cu-radiation, Bragg Brentano Optics, 40 kV, 40 mA, steps 0.01°, time 2 seconds, cut-off 40°, standard sample carrier).

EXAMPLES

The following examples describe the present invention in detail, but they are not to be construed to be in any way limiting for the present invention.

Example 1

3 g of telithromycin were dissolved in a mixture of 300 ml of acetone and water 80% (v/v $H_2O$) and the solution was spray dried with aid of a Büchi 170 apparatus at an inlet temperature of 123° C. and an outlet temperature of approximately 58° C. 1.3 g of amorphous telithromycin, as judged by XRPD, were obtained.

The sample was stressed in a closed vial at 80° C. for 24 hours. An increase in impurities of 0.2 area % was observed when measured by HPLC under the following conditions: column: symmetry C18 3.5 μm; eluent: buffer pH 4.4 (4.76 g $KH_2PO_4$ in 2000 ml $H_2O$ adjusted to pH 4.4 using $H_3PO_4$), acetonitrile (2000 ml buffer+666 ml acetonitrile); measurement at a wavelength of 205 nm; inj. Vol 5 μm; temperature 40° C.

Example 2

300 mg of telithromycin were dissolved in 10 ml of methanol. To the solution were added 10 ml of water. The solution was then frozen using liquid nitrogen and lyophilized. The obtained amorphous telithromycin was then analyzed by XRPD. The obtained spectrum is shown in FIG. 1.

Example 3

150 mg of telithromycin were dissolved in 2 ml of methanol. The solution was added to 50 ml of water.

A suspension was formed. After standing for 24 hours at ambient temperature the solid was isolated by filtration and dried in vacuo at ambient temperature. Amorphous telithromycin, as judged by XPRD, was obtained.

The invention claimed is:

1. Process for the production of stable amorphous telithromycin, comprising the steps of a) dissolving crystalline telithromycin in a solvent to form a solution and b1) adding an antisolvent to the solution obtained from step a) to form a precipitate or b2) adding the solution obtained from step a) to an antisolvent to form a precipitate and c) isolating stable amorphous telithromycin.

2. Process according to claim 1, wherein the solvent is selected from the group of $C_1$-$C_4$ alcohols, ketones, ethers, esters, aromatic hydrocarbons, chlorinated hydrocarbons, organic amides or dimethylsulfoxide and the antisolvent is water or an aliphatic acyclic or cyclic hydrocarbon.

3. Process according to claim 1, wherein the solvent is selected from $C_1$-$C_4$ alcohols, ketones, ethers, organic amides or dimethylsulfoxide and the antisolvent is water or an aliphatic acyclic or cyclic hydrocarbon.

4. Process according to claim 1, wherein the solvent is selected from aromatic hydrocarbons, chlorinated hydrocarbons or esters and the antisolvent is an aliphatic acyclic or cyclic hydrocarbon.

5. Process for the production of stable amorphous telithromycin, comprising the steps of a) dissolving crystalline telithromycin in a solvent to form a solution and b) lyophilizing the solution after addition of water to obtain stable amorphous telithromycin.

6. Process according to claim 5, wherein the solvent is selected from $C_1$-$C_4$ alcohols, ketones, ethers or mixtures thereof optionally in combination with water.

7. Process for the production of stable amorphous telithromycin, comprising the steps of a) dissolving crystalline telithromycin in a solvent to form a solution and b) spray drying the solution in the presence of water to obtain stable amorphous telithromycin.

8. Process according to claim 7, wherein the solvent is selected from $C_1$-$C_4$ alcohols, ketones and ethers or mixtures thereof optionally in combination with water.

9. Process according to claim 7, wherein a pharmaceutical carrier is present.

* * * * *